(12) United States Patent
Kim et al.

(10) Patent No.: US 10,085,950 B2
(45) Date of Patent: Oct. 2, 2018

(54) PHARMACEUTICAL COMPOSITION FOR CANCER TREATMENT CONTAINING GOSSYPOL AND PHENFORMIN AS ACTIVE INGREDIENTS

(71) Applicant: NATIONAL CANCER CENTER, Gyeonggi-do (KR)

(72) Inventors: Soo Youl Kim, Gyeonggi-do (KR); Jong Heon Kim, Gyeonggi-do (KR); Young Ki Bae, Gyeonggi-do (KR); Ho Lee, Gyeonggi-do (KR); Hyon Chol Jang, Seoul (KR); Yong-Doo Choi, Gyeonggi-do (KR); Kyeong Man Hong, Gyeonggi-do (KR); Dong Wan Hong, Gyeonggi-do (KR)

(73) Assignee: National Cancer Center, Goyang-Si (KR)

(*) Notice: Subject to any disclaimer, the term of this patent is extended or adjusted under 35 U.S.C. 154(b) by 0 days.

(21) Appl. No.: 15/121,838

(22) PCT Filed: Feb. 26, 2015

(86) PCT No.: PCT/KR2015/001889
§ 371 (c)(1),
(2) Date: Aug. 26, 2016

(87) PCT Pub. No.: WO2015/130109
PCT Pub. Date: Sep. 3, 2015

(65) Prior Publication Data
US 2017/0071877 A1    Mar. 16, 2017

(30) Foreign Application Priority Data
Feb. 27, 2014    (KR) .................. 10-2014-0023315

(51) Int. Cl.
*A61K 31/11*    (2006.01)
*A61K 31/155*    (2006.01)

(52) U.S. Cl.
CPC ............ *A61K 31/11* (2013.01); *A61K 31/155* (2013.01)

(58) Field of Classification Search
CPC .............................. A61K 31/11; A61K 31/155
See application file for complete search history.

(56) References Cited

FOREIGN PATENT DOCUMENTS

| KR | 1020080097496 A | 11/2008 |
| KR | 1020110136753 A | 12/2011 |

OTHER PUBLICATIONS

Wang et al (Di-San Junyi Daxue, 2013, 35(19), 2024-2027, SciFinder Scholar Abstract Translation).*
Wang (Di-San Junyi Daxue, 2013, 35(19), 2024-2027, SciFinder Scholar Abstract Translation).*
Kalender et al ( Cell Metabolism, 2010, 11, 390-401).*
Caraci et al (Life Sciences, 2003, 74, 643-650).*
Shelley et al (Cancer Letters, 1999, 135, 171-180).*
Heist et al (Year: 2010).*
Porporato et al., "Anticancer targets in the glycolytic metabolism of tumors: a comprehensive review", Frontiers in Pharmacology. Aug. 25, 2011, vol. 2: Article 49, pp. 1-18.
Bailey et al., "Targeting the Metabolic Microenvironment of Tumors" , Adv Pharmacol. 2012: 65:63-107.
International Search Report for PCT/KR2015/001889, dated May 28, 2015, 3 pages.

* cited by examiner

*Primary Examiner* — Kortney L. Klinkel
*Assistant Examiner* — Ibrahim D Bori
(74) *Attorney, Agent, or Firm* — Leydig, Voit & Mayer, Ltd.

(57) ABSTRACT

The present invention relates to a pharmaceutical composition for cancer treatment containing gossypol and phenformin as active ingredients. Specifically, the combinative treatment with gossypol and phenformin was verified to have a significantly higher anticancer activity than a single treatment with gossypol and phenformin alone. Therefore, the pharmaceutical composition of the present invention containing gossypol and phenformin having a synergetic anticancer activity can be favorably used for cancer treatment.

4 Claims, 11 Drawing Sheets

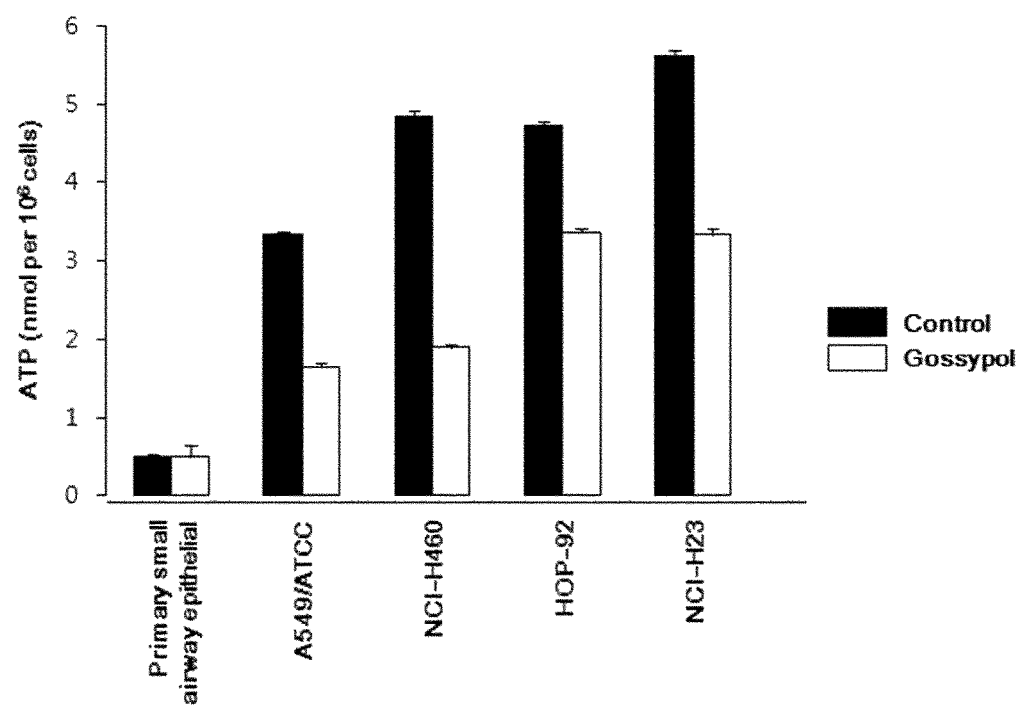
[Fig 1]

[Fig 2]
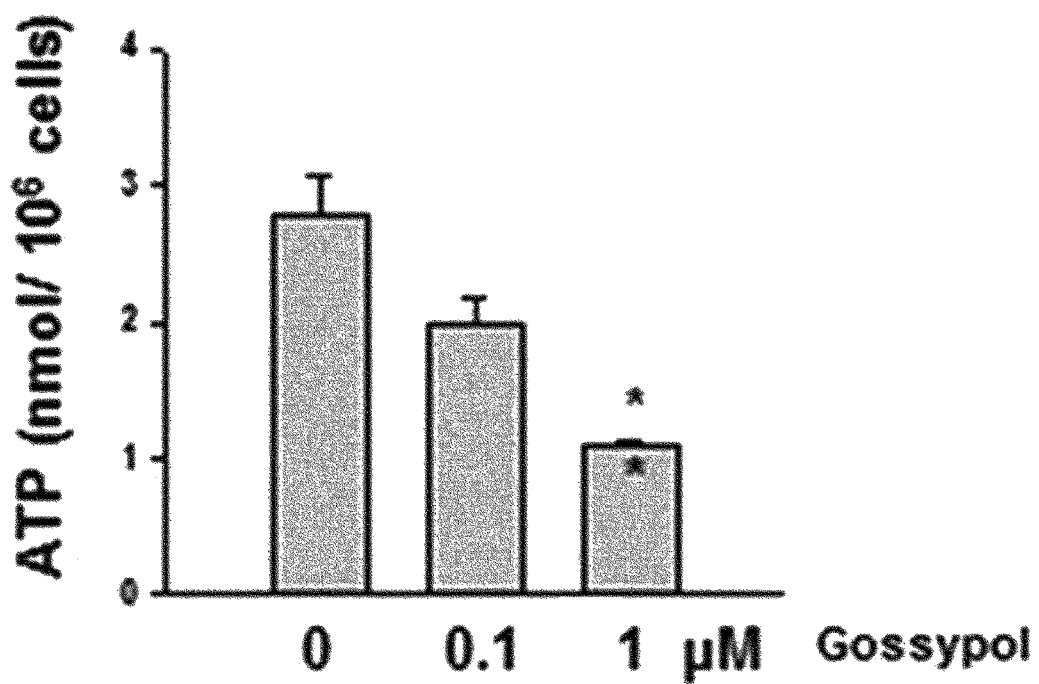

[Fig 3]
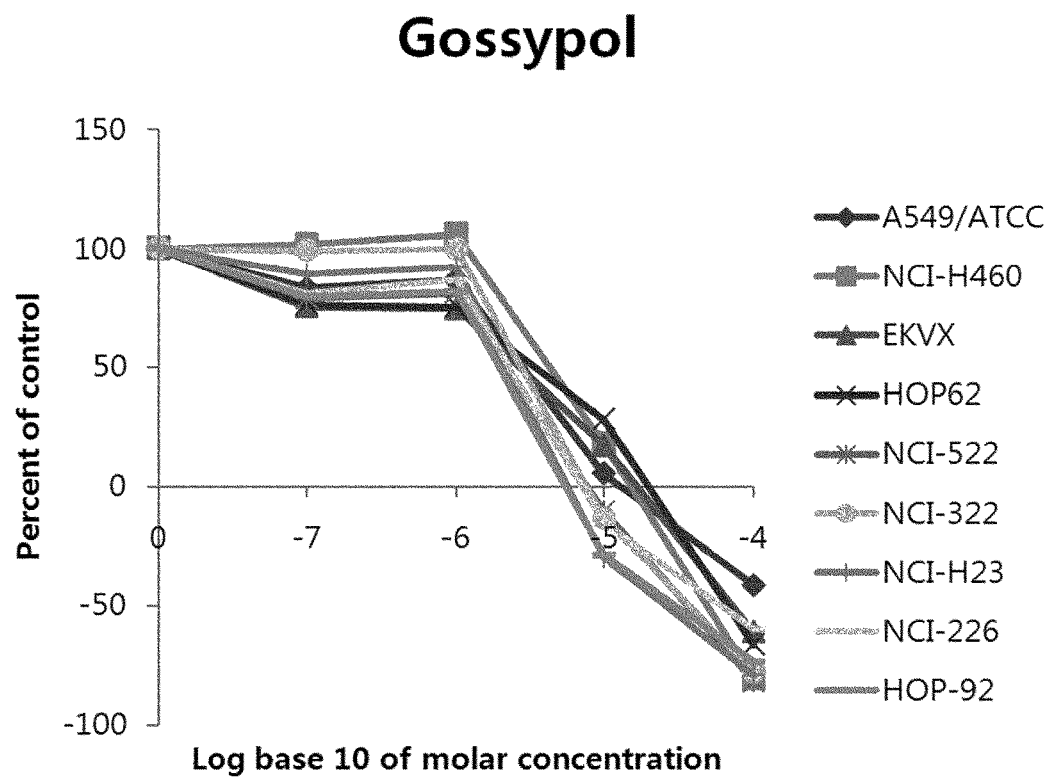

[Fig 4]
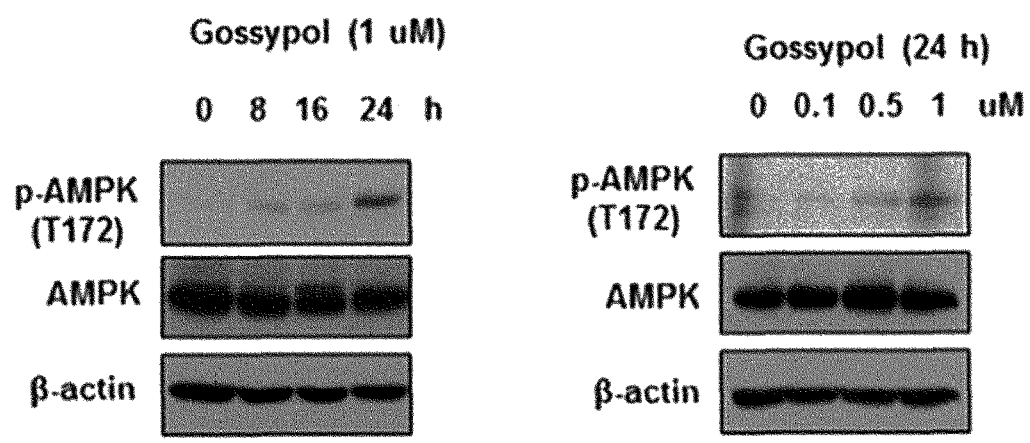

[Fig 5]
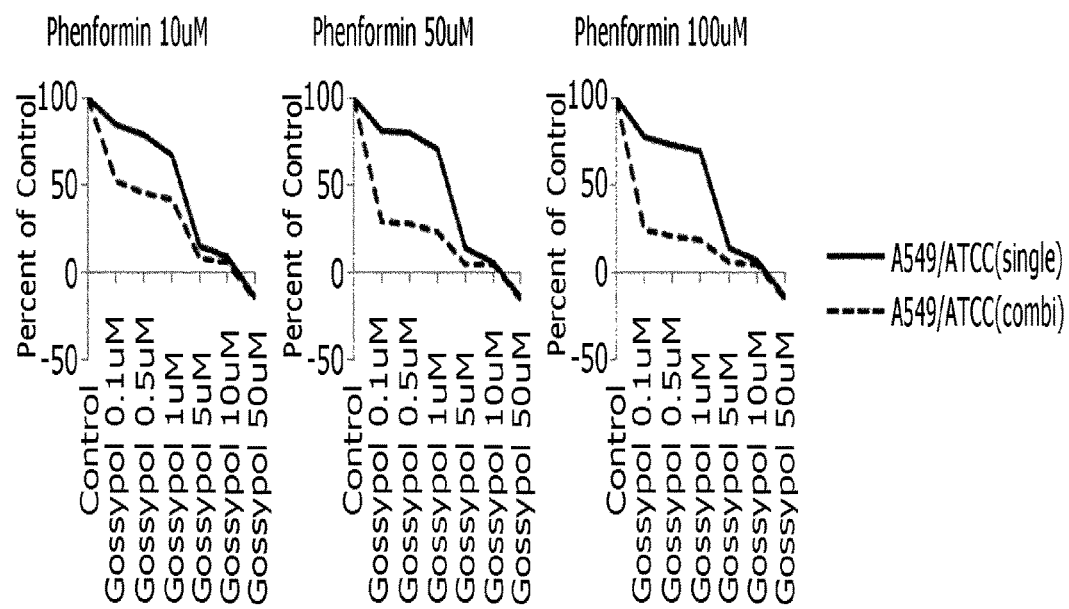

[Fig 6]
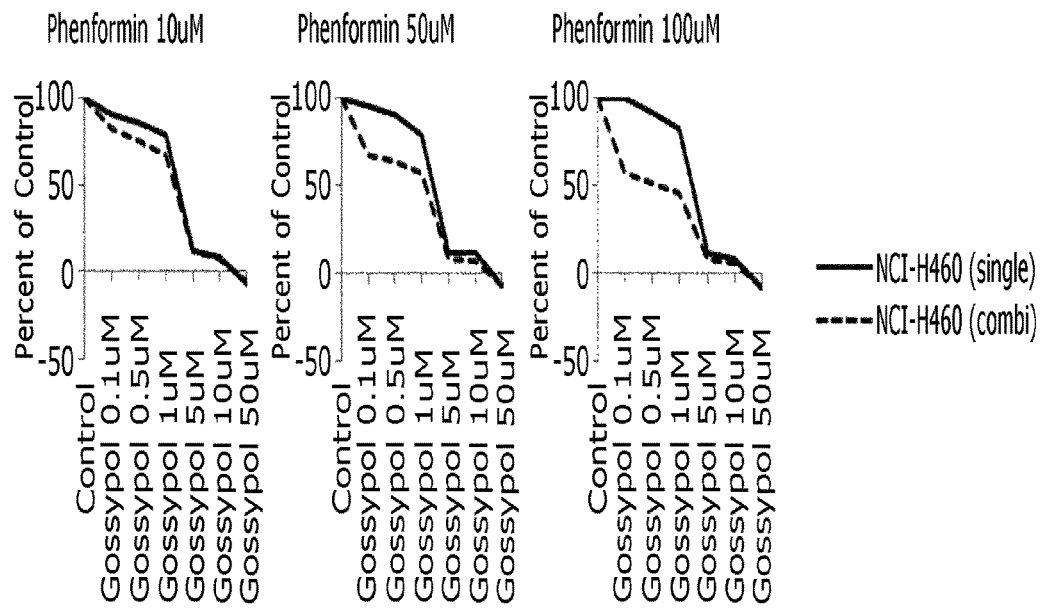

[Fig 7]
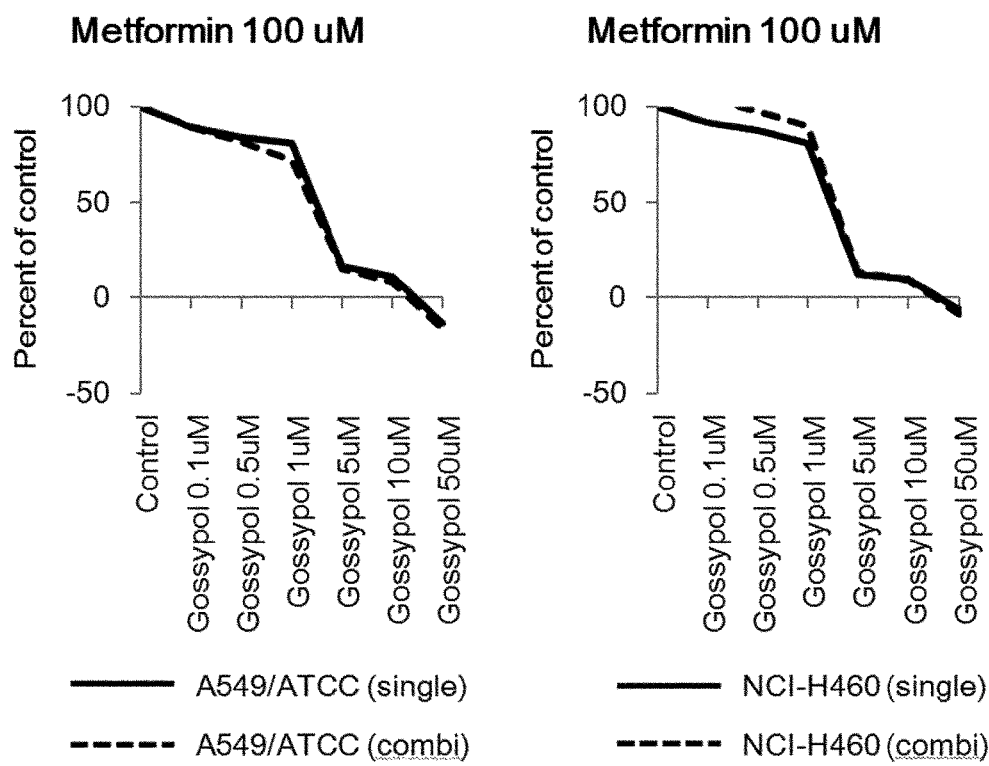

[Fig 8]
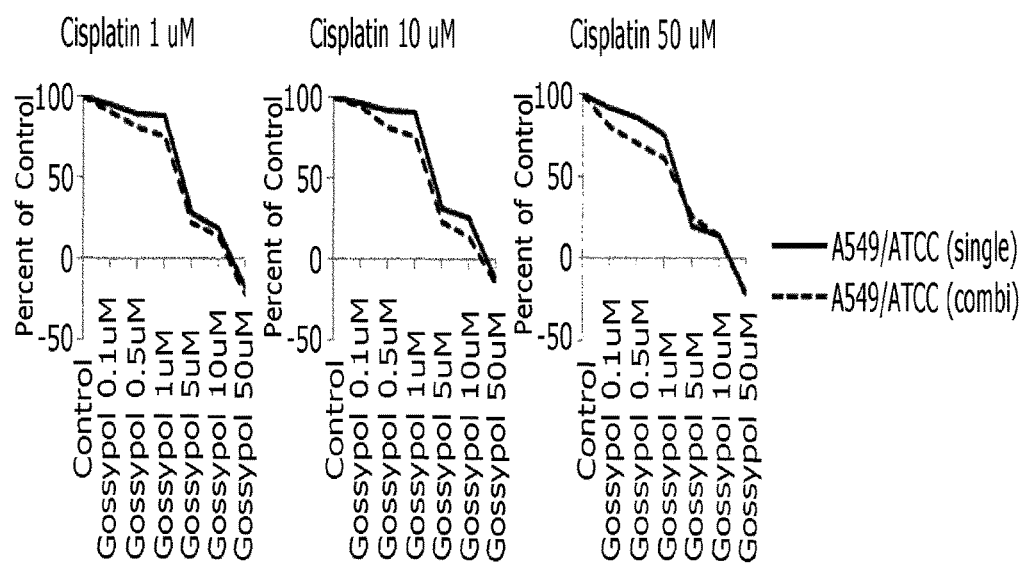

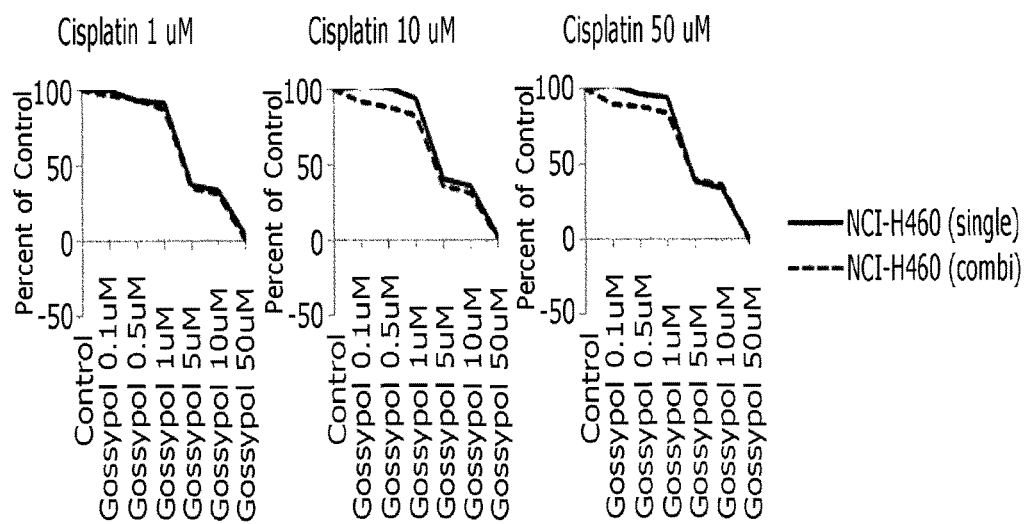
[Fig 9]

[Fig 10]
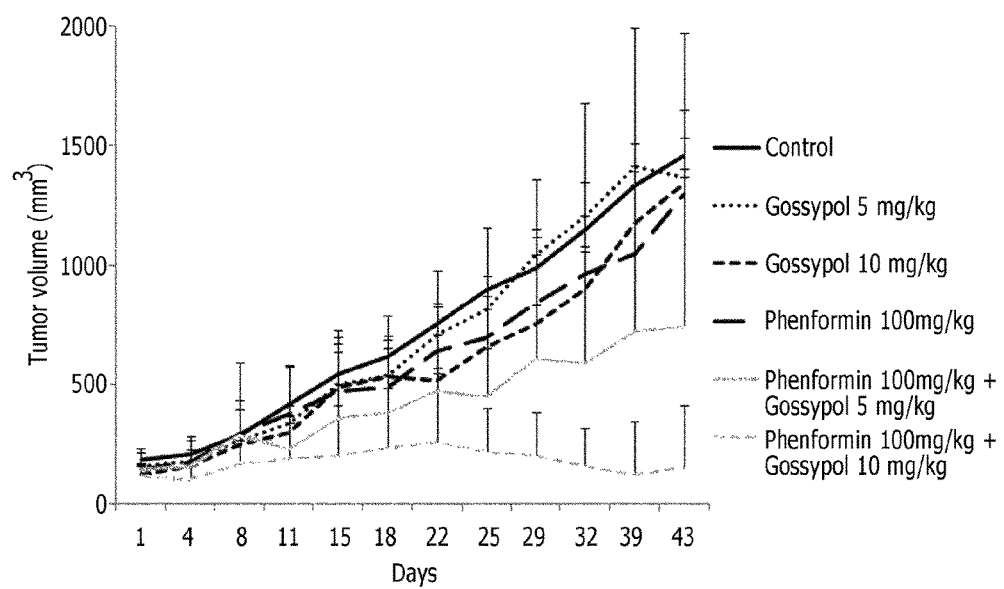

[Fig 11]
Control group vs Phenformin 100mg/kg Gossypol 10mg/kg combination group
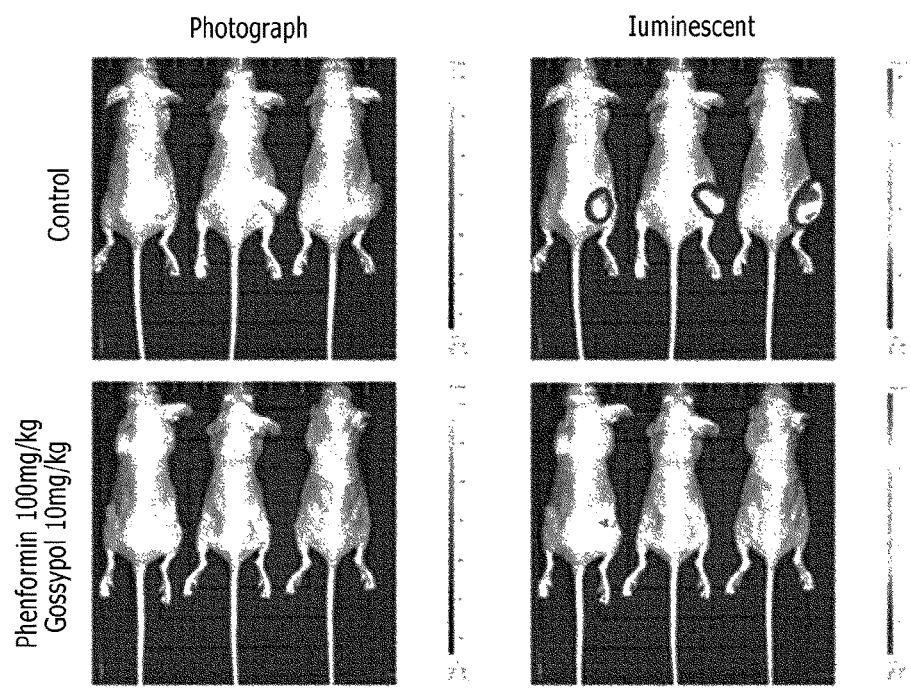

PHARMACEUTICAL COMPOSITION FOR CANCER TREATMENT CONTAINING GOSSYPOL AND PHENFORMIN AS ACTIVE INGREDIENTS

CROSS-REFERENCE TO RELATED APPLICATION

This application claims priority to and is a 35 U.S.C. § 371 national phase application of PCT/KR2015/001889 (WO2015/130109), filed on Feb. 26, 2015 entitled "Pharmaceutical Composition for Cancer Treatment Containing Gossypol and Phenformin as Active Ingredients", which application claims priority to and the benefit of Korean Patent Application No. 10-2014-0023315, filed Feb. 27, 2014; the disclosures of which is incorporated herein by reference in their entirety.

TECHNICAL FIELD

The present invention relates to a pharmaceutical composition for cancer treatment containing gossypol and phenformin as active ingredients and thus exhibiting a synergic anticancer activity, a method of treating cancer using the same, and a kit for cancer treatment.

BACKGROUND ART

An aggressive cancer cell phenotype is the result of a variety of genetic and epigenetic alterations leading to deregulation of intracellular signaling pathways (Ponder, Nature 411:336 (2001)). However, the commonality for all cancer cells, is their failure to execute an apoptotic program, and the lack of appropriate apoptosis due to defects in a normal apoptosis mechanism is a hallmark of cancer (Lowe et al., Carcinogenesis 21:485 (2000)). Most current cancer therapies encompassing chemotherapy, radiation and immunotherapy indirectly induce apoptosis in cancer cells. Therefore, the inability of cancer cells to execute an apoptotic program due to defects in a normal apoptotic mechanism is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407:810 (2000)). Accordingly, current and future efforts towards designing and developing new molecular target-specific anticancer therapies to improve survival and quality of life of cancer patients must include strategies that specifically target cancer cell resistance to apoptosis. In this regard, targeting critical negative regulators that play a central role in directly inhibiting apoptosis in cancer cells represents a highly promising therapeutic strategy for new anticancer drug design.

While studies on various cancer-targeting substances are progressing to fight cancer, in the case of terminal cancer, most of the target therapies are used to prolong life, rather to fight cancer. One of these studies shows that a variety of cancer metabolic regulators are helpful in anticancer treatment. The basis of this study is that universal metabolic characteristics specific to cancer are targeted. For example, this means that cancer cells prefer lactate fermentation rather than breakdown of glucose into carbon dioxide and water, like the Warburg effect. For this reason, when glycolysis is interrupted to reduce the Warburg effect, cancer cells are starved, and thus are harder to grow or die.

Bcl-2 family proteins are known as a class of central negative regulators in apoptosis (Adams et al., Science 281:1322 (1998); Reed, Adv. Pharmacol. 41:501 (1997); Reed et al., J. Cell. Biochem. 60:23 (1996)). Bcl-2 is a basic member of the family, and was first isolated as a product of an oncogene. The Bcl-2 family, now, encompasses both of anti-apoptotic molecules such as Bcl-2 and Bcl-XL, and pro-apoptotic molecules such as Bax, Bak, Bid and Bad. Bcl-2 and Bcl-XL are overexpressed in various types of human cancer (e.g., breast cancer, prostate cancer, colorectal cancer, lung cancer, etc.) including non-Hodgkin's lymphoma, caused by chromosomal translocations (t14, 18) inducing the overexpression of Bcl-2. This suggests that a variety of cancer cells types, depending on increased levels of Bcl-2 and/or Bcl-XL, maintain another cellular derangement such that the cancer cells are defined as cancer cells or pre-cancer cells, and attempt to carry out apoptosis pathways. Further, increased expression of the Bcl-2 family protein is recognized as the basis of the expression of resistance to radiation and cancer-therapeutic drugs inducing cell death by various pathways in tumor cells. It is considered that Bcl-2 and Bcl-XL play a role in migration and invasion, and thus metastasis of tumor cells (Amberger et al., Cancer Res. 58:149 (1998); Wick et al., FEBS Lett, 440:419 (1998); Mohanam et al., Cancer Res. 53:143 (1993); Pedersen et al., Cancer Res., 53:5158 (1993)). It seems that the Bcl-2 family protein provides tumor cells having a mechanism for existence in a new and non-replicable environment (e.g., metastatic regions), and contributes to the organospecific pattern of the spread of clinical metastatic cancer (Rubio, La Invest. 81:725 (2001); Fernandez et al., Cell Death Differ. 7:350 (2000)). It is further considered that anti-apoptotic proteins such as Bcl-2 and/or Bcl-XL regulate cell-cell interaction through, for example, the regulation of cell surface integrins (Reed, Nature 387:773 (1997); Frisch et al., Curr. Opin. Cell Biol. 9:701 (1997); Del Bufalo et al., FASEB J. 11:947 (1997)). For this reason, therapeutic strategies for targeting Bcl-2 and Bcl-XL in cells have been widely examined to recover cancer cells sensitivity and overcome resistance of cancer cells to apoptosis (Adams et al., Science 281:1322 (1998); Reed, Adv. Pharmacol. 41:501 (1997); Reed et al., J. Cell. Biochem. 60:23 (1996)). Currently, there are ongoing Bcl-2 antisense therapies, which are several phase III clinical trials for treating solid and non-solid tumors.

Gossypol is a double biphenolic compound naturally derived from crude cottonseed oil (*Gossypium* sp.). Clinical trials for gossypol as a male contraceptive show safety in the long-term administration of this compound (Wu, Drugs 38:333 (1989)). Also, recently, it was known that gossypol has an anti-proliferative effect (Flack et al., J. Clin. Endocrinol. Metab. 76:1019 (1993); Bushunow et al., J. Neuro-Oncol., 43:79 (1999); Van Poznak et al., Breast Cancer Res. Treat. 66:239 (2001)). It was recently shown that (−)-Gossypol and a derivative thereof are potent inhibitors of Bcl-2 and Bcl-XL, and have a powerful anticancer activity (U.S. Patent Application No. 2003/0008924).

Phenformin, which is a biguanide-based drug such as metformin, is known as an antidiabetic agent. However, as it has been known that biguanide-based drugs including phenformin are effective for treatment of p53 gene-deficient cancer by activating AMP-activated protein kinase (AMPK), which is a crucial enzyme for physiologically regulating carbohydrate metabolism and lipid metabolism, research on the anticancer effect of a phenformin drug was conducted to demonstrate the probability of the anticancer effect of phenformin (Effect of phenformin on the proliferation of human tumor cell lines. Life Sciences, 2003 Dec. 19: vol. 74 (issue 5): 643-650.; Potentiation of antitumor effect of cyclophosphamide and hydrazine sulfate by treatment with the antidiabetic agent, 1-phenylethylbiguanide (phenformin), Cancer Let. 1979 October; 7(6):357-61.). While the anticancer effect of each of the phenformin and gossypol has been known, a synergic anticancer effect of the actions of these drugs has not been known yet.

Therefore, from the result of research on the development of substances for exhibiting a more potent anticancer effect, the inventors demonstrated that the combination of gossypol as an ALDH inhibitor and biguanide-based phenformin exhibits a considerable synergic anticancer effect, unlike other substances, and thus completed the present invention.

DISCLOSURE

Technical Problem

An object of the present invention is to provide a pharmaceutical composition for cancer treatment containing gossypol and phenformin as active ingredients.

Another object of the present invention is to provide a use of gossypol and phenformin, or acceptable salts thereof for preparation of an anticancer drug.

Still another object of the present invention is to provide a method of treating cancer, which includes administering therapeutically effective amounts of gossypol and phenformin, or acceptable salts thereof to a subject.

Yet another object of the present invention is to provide a pharmaceutical kit for cancer treatment.

Technical Solution

To achieve the objects, the present invention provides a pharmaceutical composition containing gossypol and phenformin, or acceptable salts thereof as effective components for cancer treatment.

The present invention further provides a use of gossypol and phenformin, or acceptable salts thereof for preparation of an anticancer drug.

The present invention further provides a method of treating cancer, which includes administering therapeutically effective amounts of gossypol and phenformin, or acceptable salts thereof to a subject.

The present invention further provides a pharmaceutical kit for cancer treatment, which contains two separated components as follows:
a) gossypol or an acceptable salt thereof, and
b) phenformin or an acceptable salt thereof.

Advantageous Effects

According to the present invention, as compared to single treatment, combination treatment of gossypol having no apoptotic effect on cancer cell lines or a weak inhibitory effect against ALDH and phenformin lowering mitochondrial oxidative phosphorylation exhibits a considerable anticancer effect, and therefore a pharmaceutical composition containing gossypol and phenformin as active ingredients of the present invention can be useful in cancer treatment.

DESCRIPTION OF DRAWINGS

FIG. 1 shows the inhibition of ATP production in cancer cells by gossypol treatment:

Primary small airway epithelial: normal lung epithelial cells (control).

FIG. 2 shows the inhibition of ATP production in cancer cells by treatment of 0, 0.1 or 1 μM gossypol.

FIG. 3 shows the result of an SRB test for 9 types of lung cancer cell lines:
0: control not treated with gossypol;
−7: treatment of $10^{-7}$M (0.1 μM) gossypol;
−6: treatment of $10^{-6}$M (1 μM) gossypol;
−5: treatment of $10^{-5}$M (10 μM) gossypol; and
−4: treatment of $10^{-4}$M (100 μM) gossypol.

FIG. 4 shows AMPK phosphorylation by gossypol over time or by concentration in A549 lung cancer cell lines:
p-AMPK (T172): phosphorylated AMPK;
AMPK: total amount of AMPK; and
β-actin: control.

FIG. 5 shows the growth of cancer cell lines by the treatment of 0.1 μM, 0.5 μM, 1 μM, 5 μM, 10 μM or 50 μM gossypol, while 10 μM, 50 μM or 100 μM phenformin is treated individually:
solid line: growth curve of cancer cells with single treatment of phenformin to A549/ATCC cell line;
dotted line: growth curve of cancer cells with combination treatment of phenformin and gossypol to A549/ATCC cell line; and
Control: cancer cells treated with neither gossypol nor phenformin.

FIG. 6 shows the growth of cancer cell lines by the treatment of 0.1 μM, 0.5 μM, 1 μM, 5 μM, 10 μM or 50 μM gossypol, while 10 μM, 50 μM or 100 μM phenformin is treated individually:
solid line: growth curve of cancer cells with single treatment of phenformin to NCI-H460 cell line;
dotted line: growth curve of cancer cells with combination treatment of phenformin and gossypol to NCI-H460 cell line; and
Control: cancer cells with treatment of neither gossypol nor phenformin.

FIG. 7 shows the growth of cancer cell lines by the treatment of 0.1 μM, 0.5 μM, 1 μM, 5 μM, 10 μM or 50 μM gossypol individually, while 100 μM metformin is treated:
left graph, solid line: growth curve of cancer cells with single treatment of metformin to A549/ATCC cell line;
left graph, dotted line: growth curve of cancer cells with combination treatment of metformin and gossypol to A549/ATCC cell line;
right graph, solid line: growth curve of cancer cells with single treatment of metformin to NCI-H460 cell line;
right graph, dotted line: growth curve of cancer cells with combination treatment of metformin and gossypol to NCI-H460 cell line; and
Control: cancer cells with treatment of neither gossypol nor metformin.

FIG. 8 shows the growth of cancer cell lines by the treatment of 0.1 μM, 0.5 μM, 1 μM, 5 μM, 10 μM or 50 μM gossypol, while 1 μM, 10 μM or 50 μM cisplatin is treated individually:
solid line: growth curve of cancer cells with single treatment of cisplatin to A549/ATCC cell line;
dotted line: growth curve of cancer cells with combination treatment of cisplatin and gossypol to A549/ATCC cell line; and
Control: cancer cells with treatment of neither gossypol nor cisplatin.

FIG. 9 shows the growth of cancer cell lines by the treatment of 1 μM, 10 μM or 50 μM cisplatin, while 0.1 μM, 0.5 μM, 1 μM, 5 μM, 10 μM or 50 μM gossypol is treated individually:

solid line: growth curve of cancer cells with single treatment of cisplatin to NCI-H460 cell line;

dotted line: growth curve of cancer cells with combination treatment of cisplatin and gossypol to NCI-H460 cell line; and Control: cancer cells with treatment of neither gossypol nor cisplatin.

FIG. 10 shows the tumor size and tumor-reducing effect evaluated in tumor-bearing mice to which gossypol and/or phenformin are administered.

FIG. 11 shows the tumor sizes of a mouse group co-treated with 100 mg/kg of phenformin and 10 mg/kg of gossypol and a control.

MODES OF THE INVENTION

Hereinafter, the present invention will be described in detail.

The present invention provides a pharmaceutical composition for cancer treatment, which contains gossypol and phenformin as active ingredients.

The gossypol may be a compound of Formula 1 or a derivative thereof, but the present invention is not limited thereto:

[Formula 1]

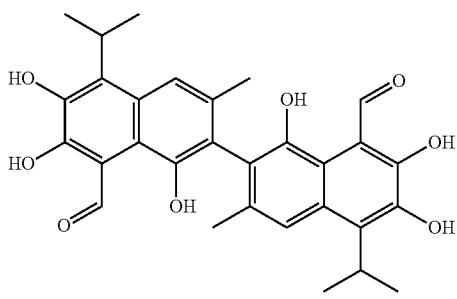

The phenformin may be a compound of Formula 2 or a derivative thereof, but the present invention is not limited thereto:

[Formula 2]

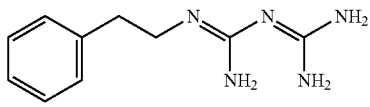

The pharmaceutical composition may comprise gossypol and phenformin, or acceptable salts thereof, but the present invention is not limited thereto.

The concentration of gossypol may be, but is not limited to, 0.1 nM to 100 μM.

The concentration of phenformin may be, but is not limited to, 1 to 200 μM.

The cancer may be any one selected from the group consisting of uterine cancer, breast cancer, stomach cancer, brain cancer, rectal cancer, colon cancer, lung cancer, skin cancer, hematological cancer and liver cancer, preferably, lung cancer, and most preferably, small cell lung cancer.

However, the pharmaceutical composition of the present invention can be applied to any type of cancer since it targets a specific metabolism of cancer cells, and therefore, the present invention is not limited to the above-listed examples.

The pharmaceutical composition for cancer treatment may simultaneously release phenformin and gossypol, or may release either phenformin or gossypol first.

Throughout the specification, the term "pharmaceutical composition" should be interpreted, unless particularly defined otherwise, to encompass a single dose type such as an oral drug or injection taken or administered once in addition to a plurality of unit dosage forms divided into two or more times when administered. For example, the term "pharmaceutical composition containing gossypol and phenformin" should be interpreted to include a single unit dosage form including both active ingredients in addition to two unit dosage forms including respective active ingredients. Also, the term "pharmaceutical composition containing gossypol and phenformin" may encompass a single or two unit dosage forms even when a single unit dosage form including both active ingredients is prepared to be released with a time lag and simultaneously administered, or two unit dosage forms are simultaneously administered or administered at intervals of a predetermined time or less, resulting in a synergic action between the two active ingredients included together in respective unit dosage forms in a living body, and thus included within the scope of the "pharmaceutical composition for cancer treatment containing gossypol and phenformin as active ingredients." Both active ingredients may be released or treated (or administered) simultaneously or with a time lag. Accordingly, the pharmaceutical composition for cancer treatment, which contains the gossypol and phenformin, or pharmaceutically acceptable salts thereof as active ingredients, may be a simple combination pharmaceutical composition enabling simultaneous combination treatment (or release) or a pharmaceutical composition enabling combination treatment (or release) with a time lag.

Throughout the specification, the term "time-lag release or time-lag administration" refers to release or administration of a drug such that active ingredients that are individually taken or administered are not simultaneously but sequentially absorbed. Such "time-lag release or time-lag administration" may be realized in a combination formulation in which two ingredients are included in one dosage form, or a formulation or dosage unit which is designed to enable time-lag release of at least one ingredient even when individual active ingredients are prepared in respective single formulations, thereby exhibiting an effect of a time lag though the ingredients which are simultaneously taken or administered. Also, the "time-lag administration" may also include a method of administering two active ingredients at regular intervals.

Throughout the specification, the term "acceptable salt" is intended to refer to a salt which retains a biological effect of a specific compound, and a pharmaceutically acceptable salt is widely known to those of ordinary skill in the art.

In the pharmaceutical composition, gossypol and phenformin may be used as they are, but a derivative thereof may be prepared, in consideration of solubility and stability.

The pharmaceutical composition of the present invention may further comprise an anticancer agent, but the present invention is not limited thereto.

The anticancer agent may be, but is not limited to, at least one drug selected from nitrogen mustard, iniboxaliplatin, rituximab, erlotinib, neratinib, lapatinib, gefitinib, vandetanib, nilotinib, semaxanib, bostutinib, axitinib, cediranib, lestaurtinib, trastuzumab, gefitinib, bortezomib, sunitinib, carboplatin, sorafenib, bevacizumab, cisplatin, cetuximab, *Viscum album,* asparaginase, tretinoin, hydroxycarbamide, dasatinib, estramustine, gemtuzuabozogamicin, ibritumomabtiuxetan, heptaplatin, methyl aminolevulinic acid, amsacrine, alemtuzumab, procarbazine, alprostadil, holmium nitrate.chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, navelbine, fadrozole, tamoxifen, toremifene, testolactone, anastrozole, letrozole, vorozole, bicalutamide, lomustine and carmustine.

Meanwhile, the pharmaceutical composition of the present invention may comprise one or more types of pharmaceutically acceptable carriers, other than the above-described active ingredients. The term "pharmaceutically acceptable carrier" used herein refers to a pharmaceutical additive that is useful in the formulation of a pharmaceutical composition for administration in a suitable dosage form, and is non-toxic and non-sensitive under usage conditions, and a specific content ratio of such a carrier may be determined according to standard pharmaceutical practice, as well as solubility, chemical property or selected administration route of an active ingredient. Also, the pharmaceutical composition of the present invention may further comprise a pharmaceutically acceptable additive, and examples of the pharmaceutically acceptable additive may comprise starch, gelatinized starch, microcrystalline cellulose, lactose, povidone, colloidal silicon dioxide, calcium hydrogen phosphate, lactose, mannitol, taffy, Arabic gum, pregelatinized starch, corn starch, powdery cellulose, hydroxypropylcellulose, Opadry, sodium starch glycolate, Carnauba wax, synthetic aluminum silicate, stearic acid, magnesium stearate, aluminum stearate, calcium stearate, sucrose, dextrose, sorbitol and talc. The pharmaceutically acceptable additive according to the present invention may be included at 0.1 to 90 parts by weight with respect to the composition, but the present invention is not limited thereto.

The pharmaceutical composition of the present invention may be administered in various oral and parenteral forms in actual clinical administration, and in preparation, may be formulated with typically used diluting agents or excipients such as a filler, a thickening agent, a binder, a wetting agent, a dispersant, a surfactant, etc. Examples of a solid oral formulation may include a tablet, a pill, powder, a granule, and a capsule, and such a solid preparation may be formulated by mixing at least one excipient, for example, starch, calcium carbonate, sucrose, lactose or gelatin, with a Pueraria extract. Also, rather than a simple excipient, lubricants such as magnesium stearate talc may be used. A liquid oral formulation may be a suspension, a liquid for internal use, an emulsion and a syrup, and contain various excipients, for example, a wetting agent, a sweetener, a flavoring agent, and a preservative, in addition to a frequently used simple diluent such as water or liquid paraffin. Examples of a parenteral formulation may include a sterilized aqueous solution, a non-aqueous solvent, a suspension, an emulsion, a lyophilizing agent, and a suppository. As a non-aqueous solvent or suspension agent, propylene glycol, polyethylene glycol, a vegetable oil such as olive oil, or an injectable ester such as ethylolate may be used. As the base of a suppository, Witepsol, Macrogol, Tween 61, cacao butter, laurin fat or glycerogelatin may be used.

The pharmaceutical composition of the present invention may be orally or parenterally administered according to a desired method, and for parenteral administration, topical use for skin, intraperitoneal, intrarectal, subcutaneous, intravenous, intramuscular, or intracardial injection may be used. The dose of the pharmaceutical composition of the present invention may vary depending on the patient's body weight, age, sex, health condition, diet, administration time, administration route, excretion rate and disease severity.

The dose of the pharmaceutical composition of the present invention may vary depending on the patient's body weight, age, sex, health condition, diet, administration time, administration route, excretion rate and disease severity, and may be administered at 0.0001 to 100 mg/kg, preferably, 0.001 to 10 mg/kg once or six times a day, based on the amount of the Pueraria extract.

For treatment of a cancer patient, the pharmaceutical composition of the present invention may be used individually or in combination with surgery, hormone treatment, drug treatment and a biological reaction regulator.

A subject to which the present invention can be applied may be a mammal, preferably, a human or a non-human mammal, and most preferably, a human.

Also, the present invention provides a use of gossypol and phenformin, or acceptable salts thereof for preparation of an anticancer drug.

The cancer may be any one selected from the group consisting of uterine cancer, breast cancer, stomach cancer, brain cancer, rectal cancer, colon cancer, lung cancer, skin cancer, hematological cancer and liver cancer, preferably, lung cancer, and most preferably, small cell lung cancer. However, the pharmaceutical composition of the present invention can be applied to any type of cancer since it targets a specific metabolism of cancer cells, and therefore, the present invention is not limited to the above-listed examples.

Also, the present invention provides a method of treating cancer, which comprises administering a therapeutically effective amount of gossypol and phenformin, or acceptable salts thereof to a subject.

The term "therapeutically effective amount" used herein refers to the amount sufficient for inhibiting cancer cells.

The subject may be a patient with cancer to be treated, preferably a human, but the present invention is not limited thereto.

The cancer may be any one selected from the group consisting of uterine cancer, breast cancer, stomach cancer, brain cancer, rectal cancer, colon cancer, lung cancer, skin cancer, hematological cancer and liver cancer, preferably, lung cancer, and most preferably, small cell lung cancer. However, the pharmaceutical composition of the present invention can be applied to any type of cancer since it targets a specific metabolism of cancer cells, and therefore, the present invention is not limited to the above-listed examples.

Throughout the specification, the term "cancer treatment" used herein refers to slowdown or interruption of cancer development. The cancer treatment includes treatment and/or relief of the symptoms of cancer.

Throughout the specification, the term "therapeutically effective amount" used herein refers to the amount sufficient for providing a therapeutic effect to a subject. Therefore, the therapeutically effective amounts of gossypol and phenformin, or acceptable salts thereof may be the amounts sufficient for treating cancer when administered to a subject with cancer.

Throughout the specification, the term "subject" or "patient" used herein may be a mammal, preferably, a human or a non-human mammal, and most preferably, a human.

Also, the present invention provides a pharmaceutical kit for cancer treatment, which contains two separated ingredients consisting of the following components:
 a) gossypol or an acceptable salt thereof, and
 b) phenformin or an acceptable salt thereof.

The cancer may be any one selected from the group consisting of uterine cancer, breast cancer, stomach cancer, brain cancer, rectal cancer, colon cancer, lung cancer, skin cancer, hematological cancer and liver cancer, preferably, lung cancer, and most preferably, small cell lung cancer. However, the pharmaceutical composition of the present invention can be applied to any type of cancer since it targets a specific metabolism of cancer cells, and therefore, the present invention is not limited to the above-listed examples.

The components a) and b) of the kit of parts may be packaged in one or more containers, each component included in the kit being packaged in each container. Suitable packaging and instructions will be provided with the kit.

The kit may include the gossypol or an acceptable salt thereof in a first unit dosage form, and the phenformin or an acceptable salt thereof in a second unit dosage form.

Hereinafter, to help in understanding the present invention, the present invention will be described in detail with reference to examples and comparative examples. However, the following examples and comparative examples are merely provided to exemplify the descriptions of the present invention, and thus the scope of the present invention is not limited by them. The examples and comparative examples of the present invention are provided to more fully explain the present invention to those of ordinary skill in the art.

EXAMPLE 1

Examination of Anticancer Activity of Gossypol

<1-1> Examination of Inhibition of Energy Generation in Cancer Cells

To examine whether energy generation in cancer cells was inhibited by gossypol, which is ALDH, non-small cell lung cancer (NSCLC) cell lines, for example, an A549 cell line, an H460 cell line, an Hop-92 cell line and an H23 cell line, were treated with 1 µM gossypol for 1 hour, followed by measuring ATP levels using an ATP assay kit (Biovision; #K354-100). As a control, normal lung epithelial cells were used.

Also, to investigate a change of ATP levels according to the concentration of gossypol, an A549 cell line was treated with 0, 0.1 or 1 µM gossypol for 1 hour, followed by measuring ATP levels.

As a result, it can be seen that the levels of ATP production (1 to 6 nmol per $1\times10^6$ cells) increased in the cancer cell lines were inhibited by gossypol (FIG. 1), and the inhibition of the ATP production was dependent on the concentration of gossypol (FIG. 2).

<1-2> Examination of Inhibition of Cancer Cell Growth

An SRB analysis was performed to examine the effect of gossypol on inhibiting the growth of cancer cell lines. Specifically, according to the doubling time of lung cancer cell lines, for example, A549/ATCC, HOP-62, HOP-92, NCI-H23, NCI-H460 or NCI-H522 cell lines, 5000 to 40000 cells were seeded per well and grown in a 96-well microtiter plate. After 24 hours, the cells were treated with 100 ml of 0, 0.1, 1, 10 or 100 µM gossypol per well, and incubated at 37° C. for 48 hours. Subsequently, 50 ml of 50% cold (4° C.) trichloroacetic acid (TCA) was added to each of the attached cell lines, and 50 ml of 80% TCA was added to each of the suspended cell lines to fix the cells. Following the incubation of the plate at 4° C. for 1 to 3 hours, the TCA solution in the plate was discarded, and then the plate was rinsed with distilled water five times. The plate was dried at room temperature for approximately 12 to 24 hours, and then fixed cells were stained with 100 ml of sulforhodamine B (SRB) at room temperature for 5 minutes. After staining, the plate was washed with 1% glacial acetic acid three times, and dried at room temperature for approximately 12 to 24 hours. The SRB dye was dissolved with 10 mM Trizma base, and an optical density was measured at 515 nm. The effect of gossypol on inhibiting cancer cells was represented as 50% growth inhibition (GI50).

As a result, it was seen that the GI50 concentration of gossypol at which the growth of the lung cancer cell lines was inhibited is 5 µM (FIG. 3).

<1-3> Effect of Gossypol on Inhibiting Cancer Cell Proliferation According to Treatment Time or Concentration of Gossypol To examine the anticancer effect according to the treatment time or concentration of gossypol, A549 lung cancer cell lines were treated with 1 µM gossypol for 0, 8, 16 or 24 hours, and then the phosphorylation of an AMP-activated protein kinase (AMPK), which is a critical protein for cancer cell division, was analyzed by western blotting.

Also, after the individual treatment of 0, 0.1, 0.5 or 1 µM gossypol for 24 hours, AMPK phosphorylation was also analyzed by western blotting.

As a result, it can be seen that the AMPK phosphorylation was increased depending on the treatment time and concentration of gossypol (FIG. 4). Consequently, it can be seen that gossypol inhibits biosynthesis that is absolutely necessary for the division of cancer cells, which is critical evidence showing that gossypol inhibits the proliferation of cancer cells.

EXAMPLE 2

Examination of Anticancer Effect According to Co-Treatment of Gossypol and Phenformin Cancer cell lines A549/ATCC and NCI-H460 were single-treated with 0.1, 0.5, 1.0, 5, 10 or 50 µM gossypol, and treated in combination with 10, 50 or 100 µM phenformin, respectively, followed by SRB analysis in the same manner as in Example <1-2>.

As a result, it was seen that in the single treatment of gossypol, the growth of the cancer cells was hardly inhibited, but in the combination treatment of phenformin and gossypol, the growth of the cancer cells was inhibited at a considerably lower concentration than 5 µM, which is the concentration of inhibiting the growth of cancer cells (GI50) in the single treatment of gossypol (FIGS. 5 and 6). Accordingly, a synergic effect of the combination treatment of phenformin and gossypol on inhibiting the growth of cancer cells was confirmed.

EXAMPLE 3

Examination of Anticancer Effect by Combination Treatment of Gossypol and Phenformin in Animal Models A549-luciferase cells were treated with 0.12% trypsin and 0.008% EDTA (T/E), detached from a plate, washed with cold PBS, and then injected into Balb/c-nude 6 week-old female mice at $2 \times 10^6$ cells/head/100 µl PBS. After one month, when a tumor size reached 100 mm³, the mice were divided into groups (five mice each), and then subjected to oral administration of phenformin at 100 mg/kg/100 µl PBS and/or gossypol at 0, 5 or 10 mg/kg/100 µl PBS (40% EtOH) five times a week. The tumor size was measured twice a week.

As a result, it was seen that, compared with the mice treated with each of gossypol and phenformin, the mice co-treated with gossypol and phenformin show a considerable decrease in tumor size (FIGS. 10 and 11).

COMPARATIVE EXAMPLE 1

Examination of Anticancer Effect by Combination Treatment of Gossypol and Different Biguanide-Based Compound To examine whether a synergic anticancer effect is only caused by the combination treatment of gossypol and phenformin, cancer cell lines A549/ATCC and NCI-H460 were single-treated with 0.1, 0.5, 1.0, 5, 10 or 50 µM gossypol, respectively, and treated in combination with 100 µM metformin, which is in a biguanide-based group including phenformin among inhibitors of mitochondrial oxidative phosphorylation and known to have an anticancer effect, and then the effect of inhibiting the cancer cell growth in each sample was examined by the same method as described above.

As a result, it can be seen that, the combination treatment of 100 µM metformin with gossypol has no significant difference from the single treatment of gossypol, and unlike the combination treatment of gossypol and phenformin, has no synergic effect (FIG. 7). Therefore, a substance having a synergic anticancer effect in combination with gossypol is considered a phenformin-based substance.

COMPARATIVE EXAMPLE 2

Examination of Anticancer Effect by Combination Treatment of Gossypol and Conventional Anticancer Agent A synergic anticancer effect was examined after cisplatin, which is commercially used as an anticancer drug in clinics, is treated alone or in combination with gossypol.

As a result, although 1, 10 or 50 µM cisplatin was treated in combination with gossypol, there was no significant difference in anticancer activity from the single treatment of gossypol, and thus it can be seen that a synergic effect is not shown (FIGS. 8 and 9).

The invention claimed is:

1. A method of treating cancer, comprising:
administering a therapeutically effective amount of gossypol and phenformin, or acceptable salts thereof to a subject, wherein the cancer is lung cancer, and wherein the administration of gossypol and phenformin has a synergistic anti-tumor effect.

2. The method of claim 1, wherein the gossypol is a compound of Formula 1:

[Formula 1]

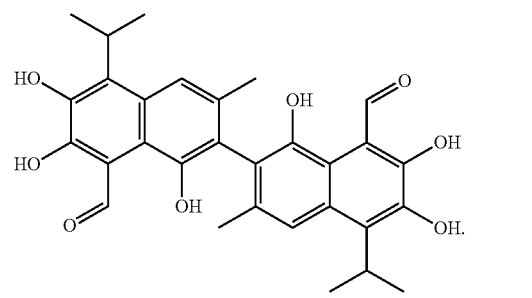

3. The method of claim 1, wherein the phenformin is a compound of Formula 2:

[Formula 2]

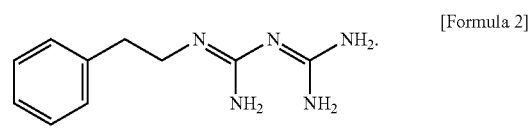 [SMILES: NC(N)=N/C(N)=N/CCc1ccccc1]

4. The method of claim 1, wherein the gossypol has a concentration of 0.1 nM to 100 µM, and the phenformin has a concentration of 1 to 200 µM.

* * * * *